US012734139B2

(12) United States Patent
Rheault et al.

(10) Patent No.: US 12,734,139 B2
(45) **Date of Patent: *Sep. 15, 2026**

(54) ENSIFENTRINE FOR DECREASING THE FREQUENCY/SEVERITY OF COPD EXACERBATIONS

(71) Applicant: Verona Pharma Limited, London (GB)

(72) Inventors: Tara Renae Rheault, Cary, NC (US); Kathleen Rickard, Durham, NC (US); Thomas Bengtsson, Lund (SE)

(73) Assignee: Verona Pharma Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/424,452

(22) Filed: Jan. 26, 2024

(65) Prior Publication Data

US 2024/0165054 A1 May 23, 2024

Related U.S. Application Data

(63) Continuation of application No. PCT/GB2023/052084, filed on Aug. 7, 2023.

(Continued)

(51) Int. Cl.

*A61K 31/137* (2006.01)
*A61K 9/00* (2006.01)

(Continued)

(52) U.S. Cl.

CPC .......... *A61K 31/137* (2013.01); *A61K 9/0078* (2013.01); *A61K 9/10* (2013.01);

(Continued)

(58) Field of Classification Search

CPC .... A61K 31/137; A61K 31/519; A61K 47/02; A61K 47/26; A61K 9/0078;

(Continued)

(56) References Cited

U.S. PATENT DOCUMENTS

| | | | |
|---|---|---|---|
| 4,482,556 | A | 11/1984 | Lal et al. |
| 5,378,818 | A | 1/1995 | Mayer et al. |

(Continued)

FOREIGN PATENT DOCUMENTS

| | | | |
|---|---|---|---|
| AU | 527997 | B2 | 3/1983 |
| DE | 43 40 981 | A1 | 6/1994 |

(Continued)

OTHER PUBLICATIONS

Cazzola et al., Ensifentrine (RPL554): an investigational PDE3/4 inhibitor for the treatment of COPD, Expert Opinion on Investigational Drugs, vol. 28, No. 10, 827-833, Sep. 1, 2019 (Year: 2019).*

(Continued)

*Primary Examiner* — Sarah Pihonak
*Assistant Examiner* — Padmaja S Rao
(74) *Attorney, Agent, or Firm* — Foley & Lardner LLP

(57) ABSTRACT

The present invention relates to a compound for use in a method for decreasing the frequency and/or severity of chronic obstructive pulmonary disease (COPD) exacerbations in a patient suffering from COPD, wherein the compound is ensifentrine or a pharmaceutically acceptable salt thereof. The present invention also relates to a compound for use in a method for treating chronic obstructive pulmonary disease (COPD) in a patient, wherein: the compound is ensifentrine or a pharmaceutically acceptable salt thereof; and the patient is susceptible to COPD exacerbations.

14 Claims, 1 Drawing Sheet

Related U.S. Application Data

(60) Provisional application No. 63/502,977, filed on May 18, 2023, provisional application No. 63/370,699, filed on Aug. 8, 2022, provisional application No. 63/370,696, filed on Aug. 8, 2022, provisional application No. 63/370,694, filed on Aug. 8, 2022.

(51) Int. Cl.

| | |
|---|---|
| ***A61K 9/10*** | (2006.01) |
| ***A61K 31/519*** | (2006.01) |
| ***A61K 31/573*** | (2006.01) |
| ***A61K 45/06*** | (2006.01) |
| ***A61K 47/02*** | (2006.01) |
| ***A61K 47/26*** | (2006.01) |
| ***A61P 11/00*** | (2006.01) |
| ***A61P 11/08*** | (2006.01) |

(52) U.S. Cl.
CPC .......... *A61K 31/519* (2013.01); *A61K 31/573* (2013.01); *A61K 45/06* (2013.01); *A61K 47/02* (2013.01); *A61K 47/26* (2013.01); *A61P 11/00* (2018.01); *A61P 11/08* (2018.01)

(58) Field of Classification Search
CPC .... A61K 31/517; A61K 31/573; A61K 45/06; A61K 9/10; A61K 2300/00; A61P 11/08; A61P 11/00
See application file for complete search history.

(56) References Cited

U.S. PATENT DOCUMENTS

| | | | |
|---|---|---|---|
| 5,985,878 | A | 11/1999 | Stokbroekx et al. |
| 6,794,391 | B2 | 9/2004 | Oxford et al. |
| 7,105,663 | B2 | 9/2006 | Oxford et al. |
| 7,378,424 | B2 | 5/2008 | Oxford et al. |
| 8,221,772 | B2 | 7/2012 | Johnson et al. |
| 8,242,127 | B2 | 8/2012 | Oxford et al. |
| 9,062,047 | B2 | 6/2015 | Walker et al. |
| 9,700,558 | B2 | 7/2017 | Walker et al. |
| 9,717,732 | B2 | 8/2017 | Walker et al. |
| 9,956,171 | B2 | 5/2018 | Spargo et al. |
| 10,463,665 | B2 | 11/2019 | Spargo et al. |
| 10,471,063 | B2 | 11/2019 | Walker et al. |
| 10,710,998 | B2 | 7/2020 | Spargo |
| 10,864,213 | B2 | 12/2020 | Abbott-Banner et al. |
| 10,945,950 | B2 | 3/2021 | Spargo et al. |
| 11,491,155 | B2 | 11/2022 | Spargo et al. |
| 11,759,467 | B2 | 9/2023 | Abbott-Banner et al. |
| 12,168,011 | B2 | 12/2024 | Spargo et al. |
| 12,194,045 | B1 | 1/2025 | Spargo et al. |
| 12,251,384 | B1 | 3/2025 | Spargo et al. |
| 12,409,180 | B2 | 9/2025 | Spargo et al. |
| 2003/0036542 | A1 | 2/2003 | Oxford et al. |
| 2003/0229108 | A1 | 12/2003 | De Belin et al. |
| 2004/0076668 | A1 | 4/2004 | Berchielli et al. |
| 2004/0171828 | A1 | 9/2004 | Oxford et al. |
| 2004/0176353 | A1 | 9/2004 | Oxford et al. |
| 2004/0247628 | A1 | 12/2004 | Lintz et al. |
| 2005/0054655 | A1 | 3/2005 | Beaulieu et al. |
| 2005/0186276 | A1 | 8/2005 | Berchielli et al. |
| 2005/0261271 | A1 | 11/2005 | Feng et al. |
| 2007/0197489 | A1 | 8/2007 | Karlsson et al. |
| 2008/0003283 | A1 | 1/2008 | Feng et al. |
| 2008/0108807 | A1 | 5/2008 | Feng et al. |
| 2008/0108808 | A1 | 5/2008 | Feng et al. |
| 2008/0113993 | A1 | 5/2008 | De Belin et al. |
| 2008/0125437 | A1 | 5/2008 | Dong et al. |
| 2008/0142759 | A1 | 6/2008 | Pays |
| 2008/0161562 | A1 | 7/2008 | Feng et al. |
| 2008/0177064 | A1 | 7/2008 | Feng et al. |
| 2008/0188501 | A1 | 8/2008 | Feng et al. |
| 2008/0199410 | A1 | 8/2008 | Johnson et al. |
| 2008/0206163 | A1 | 8/2008 | Oxford et al. |
| 2008/0254127 | A1* | 10/2008 | Watanabe ............ A61K 31/165 514/171 |
| 2009/0012059 | A1 | 1/2009 | Feng et al. |
| 2009/0075939 | A1 | 3/2009 | He et al. |
| 2010/0113413 | A1 | 5/2010 | Dong et al. |
| 2010/0204471 | A1 | 8/2010 | Tomita |
| 2011/0076276 | A1 | 3/2011 | Guo et al. |
| 2011/0190261 | A1 | 8/2011 | Dong et al. |
| 2012/0251594 | A1 | 10/2012 | Longest et al. |
| 2012/0302533 | A1 | 11/2012 | Oxford et al. |
| 2013/0078256 | A1 | 3/2013 | Guo et al. |
| 2013/0089579 | A1 | 4/2013 | Laeschke |
| 2013/0158021 | A1 | 6/2013 | Dong et al. |
| 2013/0225616 | A1 | 8/2013 | Walker et al. |
| 2014/0242174 | A1 | 8/2014 | Walker |
| 2016/0000790 | A1 | 1/2016 | Walker et al. |
| 2016/0008363 | A1 | 1/2016 | Walker et al. |
| 2017/0112839 | A1 | 4/2017 | Abbott-Banner et al. |
| 2017/0239178 | A1 | 8/2017 | Spargo et al. |
| 2017/0266190 | A1 | 9/2017 | Walker et al. |
| 2018/0021337 | A1 | 1/2018 | Spargo et al. |
| 2018/0369139 | A1 | 12/2018 | Spargo et al. |
| 2019/0282565 | A1 | 9/2019 | Liang |
| 2019/0330206 | A1 | 10/2019 | Spargo |
| 2020/0016158 | A1 | 1/2020 | Spargo et al. |
| 2021/0106585 | A1 | 4/2021 | Abbott-Banner et al. |
| 2021/0379053 | A1 | 12/2021 | Spargo et al. |
| 2022/0265549 | A1 | 8/2022 | Spargo et al. |
| 2023/0112220 | A1 | 4/2023 | Spargo et al. |
| 2024/0165023 | A1 | 5/2024 | Spargo et al. |
| 2024/0165055 | A1 | 5/2024 | Rheault et al. |
| 2024/0165117 | A1 | 5/2024 | Spargo et al. |
| 2024/0173327 | A1 | 5/2024 | Rickard et al. |
| 2024/0382489 | A1 | 11/2024 | Spargo et al. |
| 2025/0000866 | A1 | 1/2025 | Spargo et al. |
| 2025/0049781 | A1 | 2/2025 | Spargo et al. |
| 2025/0064814 | A1 | 2/2025 | Spargo et al. |
| 2025/0064815 | A1 | 2/2025 | Spargo et al. |
| 2025/0073240 | A1 | 3/2025 | Rheault et al. |
| 2025/0170135 | A1 | 5/2025 | Spargo et al. |
| 2025/0249006 | A1 | 8/2025 | Rheault |
| 2025/0249007 | A1 | 8/2025 | Spargo et al. |
| 2025/0249008 | A1 | 8/2025 | Spargo et al. |
| 2025/0319090 | A1 | 10/2025 | Spargo et al. |

FOREIGN PATENT DOCUMENTS

| | | | |
|---|---|---|---|
| DE | 19821263 | A1 | 11/1998 |
| EP | 0 601 401 | A1 | 6/1994 |
| EP | 0 876 366 | A2 | 11/1998 |
| EP | 0 983 334 | A1 | 3/2000 |
| EP | 1 305 026 | A2 | 5/2003 |
| EP | 1 418 896 | A2 | 5/2004 |
| EP | 1 438 019 | A1 | 7/2004 |
| EP | 1 519 711 | A1 | 4/2005 |
| EP | 1 586 571 | A1 | 10/2005 |
| EP | 1 651 611 | A2 | 5/2006 |
| EP | 1 993 540 | A2 | 11/2008 |
| EP | 2 063 903 | A1 | 6/2009 |
| EP | 2 167 476 | A2 | 3/2010 |
| JP | 2001-213867 | A | 8/2001 |
| JP | 3675274 | B2 | 7/2005 |
| JP | 2005-263780 | A | 9/2005 |
| KR | 101361145 | B1 | 2/2014 |
| WO | WO-97/26258 | A1 | 7/1997 |
| WO | WO-97/36039 | A1 | 10/1997 |
| WO | WO-98/45293 | A1 | 10/1998 |
| WO | WO-00/58309 | A1 | 10/2000 |
| WO | WO-0058308 | A1 | 10/2000 |
| WO | WO-01/93841 | A2 | 12/2001 |
| WO | WO-02/17894 | A2 | 3/2002 |
| WO | WO-03/000343 | A2 | 1/2003 |
| WO | WO-03/035030 | A1 | 5/2003 |
| WO | WO-03/037262 | A2 | 5/2003 |
| WO | WO-2004/004684 | A1 | 1/2004 |
| WO | WO-2005/007092 | A2 | 1/2005 |
| WO | WO-2005/007138 | A1 | 1/2005 |
| WO | WO-2005/021510 | A2 | 3/2005 |
| WO | WO-2005/095381 | A1 | 10/2005 |

(56) References Cited

FOREIGN PATENT DOCUMENTS

| | | | | |
|---|---|---|---|---|
| WO | WO-2008/036293 A1 | | 3/2008 | |
| WO | WO-2008/140553 A2 | | 11/2008 | |
| WO | WO-2009/005674 A2 | | 1/2009 | |
| WO | WO-2012020016 A1 | | 2/2012 | |
| WO | WO-2012/037782 A1 | | 3/2012 | |
| WO | WO-2012/051426 A2 | | 4/2012 | |
| WO | WO-2013/034909 A1 | | 3/2013 | |
| WO | WO-2013/034910 A1 | | 3/2013 | |
| WO | WO-2013/063468 A1 | | 5/2013 | |
| WO | WO-2013/092791 A1 | | 6/2013 | |
| WO | WO-2013/118855 A1 | | 8/2013 | |
| WO | WO-2013/128283 A2 | | 9/2013 | |
| WO | WO-2014/037726 A1 | | 3/2014 | |
| WO | WO-2014/037727 A1 | | 3/2014 | |
| WO | WO-2014140647 A1 | | 9/2014 | |
| WO | WO-2014140648 A1 | | 9/2014 | |
| WO | WO-2015173551 A1 | | 11/2015 | |
| WO | WO-2016042313 A1 | | 3/2016 | |
| WO | WO-2016128742 A1 | | 8/2016 | |
| WO | WO-2018020249 A1 | | 2/2018 | |
| WO | WO-2020074894 A1 | | 4/2020 | |
| WO | WO-2021028679 A1 | | 2/2021 | |
| WO | WO-2021150268 A1 | * | 7/2021 | ........... A61K 31/192 |
| WO | WO-2021171034 A1 | | 9/2021 | |
| WO | WO-2022261417 A1 | * | 12/2022 | ............. A61P 37/06 |
| WO | WO-2023/076205 A1 | | 5/2023 | |
| WO | WO-2023156794 A1 | | 8/2023 | |
| WO | WO-2024/033624 A1 | | 2/2024 | |
| WO | WO-2024/033625 A1 | | 2/2024 | |
| WO | WO-2024/033626 A1 | | 2/2024 | |
| WO | WO-2024/033627 A1 | | 2/2024 | |
| WO | WO-2024/084212 A1 | | 4/2024 | |
| WO | WO-2025/003643 A1 | | 1/2025 | |
| WO | WO-2025/052119 A1 | | 3/2025 | |

OTHER PUBLICATIONS

Terry et al. Inhalation Therapy for Stable COPD: 20 Years of GOLD Reports, Advances in Therapy, vol. 37, 1812-1828, Apr. 3, 2020 (Year: 2020).*

Rennard et al., Cilomilast for COPD* Results of a 6-Month, Placebo-Controlled Study of a Potent, Selective Inhibitor of Phosphodiesterase 4, Chest, vol. 129, No. 1, 56-66, Jan. 2006 (Year: 2006).*

Banner et al., Dual PDE3/4 inhibitors as therapeutic agents for chronic obstructive pulmonary disease, British Journal of Pharmacology, vol. 157, 892-906, Jun. 5, 2009 (Year: 2009).*

Ferguson., Maintenance pharmacotherapy of mild and moderate COPD: What is the Evidence?, Respiratory Medicine, vol. 105, 1268-1274, Feb. 25, 2011 (Year: 2011).*

Segal et al., Acute Exacerbations of Chronic Obstructive Pulmonary Disease, Mandell Douglas, and Bennett's Principles and Practice of Infectious Diseases, 1-50, Oct. 31, 2014 (Year: 2014).*

Abbott-Banner, K.H. et al., Dual PDE3/4 and PDE4 inhibitors: Novel treatments for COPD and other inflammatory airway diseases, Basic & Clinical Pharmacology & Toxicology, vol. 114, (2014):365-376.

Anzueto, A. et al., Treatment with Ensifentrine, a Dual PDE3 and PDE4 Inhibitor, Significantly Reduced Exacerbation Rate and Risk in Subjects with COPD: Sub-group Results from the Phase 3 Trial, ENHANCE-2 (Poster at ATS 2023—May 19-24, 2023).

Anzueto, A. et al., Treatment with ensifentrine, a dual PDE3 and PDE4 inhibitor, significantly reduced exacerbation rate and risk in subjects with COPD: sub-group results from the phase 3 trial, enhance-2, Am J Respir Crit Care Med, (2023):207:A4998.

Barjaktarevic, I. et al., Ensifentrine, a novel dual phosphodiesterase (PDE) 3 and 4 inhibitor, significantly reduces annualized exacerbations and delays the time to first exacerbation in COPD: pooled sub-group analyses of enhance-1 and enhance-2 phase 3 trials, Am J Respir Crit Care Med, (2023):207:A5008.

Barjaktarevic, I. et al., Ensifentrine, a Novel Dual Phosphodiesterase (PDE) 3 and 4 Inhibitor, Significantly Reduces Annualized Exacerbations and Delays the Time to First Exacerbation in COPD: Pooled Sub-group Analyses of ENHANCE-1 and ENHANCE-2 Phase 3 Trials (Poster at ATS 2023—May 19-24, 2023).

Breo USPI 2013.

Cazzola, M. et al., Ensifentrine (RPL554): and inhaled 'bifunctional' dual PDE3/4 inhibitor for the treatment of asthma and chronic obstructive pulmonary disease, Pharmaceutical Patent Analyst, vol. 7, 6(2018):249-257.

Daliresp USPI 2011.

Developing innovative therapies for the treatment of respiratory diseases, Nov. 2023 (presentation from Verona website).

Effect of Ensifentrine, a Novel PDE3 and PDE4 Inhibitor, on Lung Function, Symptoms and Exacerbations in Patients with COPD: The ENHANCE Trials (Presentation at ATS 2023—May 19-24, 2023).

ENHANCE-1 Phase 3 data—Dec. 2022 (presentation from Verona website).

ENHANCE-2 Phase 3 data—Aug. 2022 (presentation from Verona website).

Experimental report filed with response dated Dec. 13, 2021 to first office action on Chinese Application No. 202010090019.5, including translation of experimental report.

Experimental report filed with response dated Jan. 17, 2022 on Korean Patent Application No. 10-2017-7006862, including translation of experimental report.

Experimental report filed with response dated Jul. 4, 2022 to second office action on Chinese Application No. 202010090019.5, including translation of experimental report.

Ferguson, G.T. et al., A Dose-Ranging Study of the Novel Inhaled Dual PDE 3 and 4 Inhibitor Ensifentrine in Patients with COPD Receiving Maintenance Tiotropium Therapy, International Journal of Chronic Obstructive Pulmonary Disease, vol. 16, (2021):1137-1148.

Franciosi, L.G. et al., Efficacy and safety of RPL554, a dual PDE3 and PDE4 inhibitor, in healthy volunteers and in patients with asthma or chronic obstructive pulmonary isease: findings from four clinical trials, The Lancet. Respiratory Medicine, vol. 1, 9(2013):714-727.

Hankinson, J.L. et al., Spirometric reference values from a sample of the General U.S. Population, Am J Respir Crit Care, vol. 159, (1999):179-187.

International Search Report on PCT/GB2023/052082 dated Oct. 20, 2023.

International Search Report on PCT/GB2023/052083 dated Oct. 31, 2023.

International Search Report on PCT/GB2023/052084 dated Oct. 23, 2023.

International Search Report on PCT/GB2023/052085 dated Nov. 15, 2023.

Labiris, N.R. et al., Pulmonary drug delivery. Part II: The role of inhalant delivery devices and drug formulations in therapeutic effectiveness of aerosolized medications, Br J Clin Pharmacol., vol. 56, (2003):600-612.

Le Brun, P.P.H. et al., A review of the technical aspects of drug nebulization, Pharmacy World and Science, vol. 22, 3(2000):75-81.

Mantero, M. et al., Acute exacerbations of COPD: risk factors for failure and relapse, International Journal of COPD, vol. 12, (2017):2687-2693.

Matera, M.G. et al., Prospects for COPD treatment, Current Opinion In Pharmacology, vol. 56, (2021):74-84.

Miller, M.R. et al., Standardisation of spirometry, Eur Respir J., vol. 26, (2005):319-338.

No Author, Global Initiative for Chronic Obstructive Lung Disease (GOLD) 2022 Report.

Preparing to launch the first novel MOA in COPD in 10 years, Oct. 18, 2023 (presentation from Verona website).

Record History | ver. 42: Jul. 11, 2022 | NCT04535986 | ClinicalTrials.gov.

Record History | ver. 43: May 13, 2022 | NCT04542057 | ClinicalTrials.gov.

Rheault, T. et al., Effect of ensifentrine on lung function and health-related quality of life (QoL) by COPD severity: analysis

(56) References Cited

OTHER PUBLICATIONS from a phase 2b dose ranging study, American Journal of Respiratory and Critical Care Medicine, (2021):203:A2254.
Roca, J. et al., References values for forced spirometry, Eur Respir J., vol. 11, (1998):1354-1362.
Sciurba, F.C. et al., Ensifentrine, a novel dual phosphodiesterase (PDE) 3 and 4 inhibitor, improves lung function, symptoms, quality of life and reduces exacerbation rate and risk in patients with COPD: results from replicate phase 3 trials, Am J Respir Crit Care Med, (2023):207:A5005.
Singh, D. et al., A dose-ranging study of the inhaled dual phosphodiesterase 3 and 4 inhibitor ensifentrine in COPD, Respiratory Research, vol. 21, (2020).
Singh, D. et al., Efficacy and safety of CHF6001, a novel inhaled PDE4 inhibitor in COPD: the Pioneer study, Respir Res., vol. 21, (2020):246.
Singh, D. et al., The short-term bronchodilator effects of the dual phosphodiesterase 3 and 4 inhibitor RPL554 in COPD, Eur Respir J., vol. 52, (2018):1801074.
Spiriva Respimat USPI (US product insert), 2014.
Symbicort USPI 2006.
Taylor, N.P., Verona sets sights on PhIIb after CPOD drug comes through early trial, Fierce Biotech article, (2015).
Tudorza USPI 2012.
Verona Pharma Announces Analyses Demonstrating Ensifentrine Reduced Exacerbation Rates Across Subgroups in Phase 3 ENHANCE-2 Trial for COPD, Oct. 14, 2022 (press release from Verona website).
Zuo, H. et al., Phosphodiesterases as therapeutic targets for respiratory diseases, Pharmacology & Therapeutics, vol. 197, (2019):225-242.
Dose Ranging Study of RPL554 in Chronic Obstructive Pulmonary Disease (COPD) Patients, ClinicalTrials.gov, (2019). https://www.clinicaltrials.gov/study/NCT03443414.
U.S. Appl. No. 18/825,447, filed Sep. 5, 2024, Rheault et al.
U.S. Appl. No. 18/946,234, filed Nov. 13, 2024, Spargo et al.
U.S. Appl. No. 18/949,105, filed Nov. 15, 2024, Spargo et al.
Akers (Sterile Drug Products: Formulation, Packaging, Manufacture and Quality. Published 2010) (Year: 2010), 517 pages.
Albert, RK et al., Azithromycin for prevention of exacerbations of COPD. N. Engl. J. Med. 2011;365(8):689-98.
Anzueto, A et al., Ensifentrine, a novel phosphodiesterase 3 and 4 inhibitor for the treatment of chronic obstructive pulmonary disease: randomized, double-blind, placebo-controlled, multicenter phase III trials (the ENHANCE Trials). Am J Respir Crit Care Med. 2023;208(4):406-416.
Anzueto, A., Impact of exacerbations on COPD. Eur. Respir. Rev. 2010; 19(116):113-8.
Au, DH et al., The effects of smoking cessation on the risk of chronic obstructive pulmonary disease exacerbations. J Gen Intern Med. 2009;24(4):457-63.
Bafadhel, M et al., Predictors of exacerbation risk and response to budesonide in patients with chronic obstructive pulmonary disease : a post-hoc analysis of three randomised trials. Lancet Respir Med 2018 ; 6(2) : 117-26.
Bjermer, L. et al., Efficacy and safety of a first-in-class inhaled PDE3/4 inhibitor (ensifentrine) vs salbutamol in asthma, Pulmonary Pharmacology & Therapeutics, vol. 58, (2019).
Blasko, G. et al., Pyrimido[1,6-a]pyrido[3,4-b]indoles as new platelet inhibiting agents, European Journal of Medicinal Chemistry, vol. 21, 2 (1986):91-5.
Brat, K et al., Prognostic properties of the GOLD 2023 classification system. Int J Chron Obstruct Pulmon Dis. 2023;18:661-667.
Chen, E.H. et al., Modifications of primaquine as antimalarials. 1. 5-Phenoxy derivatives of primaquine, Journal of Medicinal Chemistry, vol. 20, 8 (1977):1107-9.
Daliresp (roflumilast). Package insert. AstraZeneca; 2020.
Dong-Sheng, M. et al., Synthesis of Daimuron, College of Chemistry and Chemical Engineering, Huaxue Yu Nianhe, vol. 6, (2003):293-295.
Dransfield, MT et al., Acute exacerbations and lung function loss in smokers with and without chronic obstructive pulmonary disease. Am J Respir Crit Care Med. 2017; 195(3):324-330.
Duffy, SP et al., Chronic obstructive pulmonary disease: evaluation and management. Med Clin North Am. 2019; 103(3):453-461.
Ferguson, G.T. et al., A Dose-Ranging Study of the Novel Inhaled Dual PDE 3 and 4 Inhibitor Ensifentrine in Patients with COPD Receiving Maintenance Tiotropium Therapy, International Journal of Chronic Obstructive Pulmonary Disease, vol. 16, (2021):1137-1148, with Supplement to Manuscript, 32 pages.
Frank, A.W., Synthesis of some carbonyl derivatives of tris(aminomethyl)phosphine oxide, Phosphorus and Sulfur and the Related Elements, vol. 22, 3(1985):265-76.
Global Initiative for Chronic Obstructive Lung Disease, 2021 Report, 2021, 54 pages.
Global strategy for the diagnosis, management, and prevention of chronic obstructive pulmonary disease 2023 report. Global Initiative for Chronic Obstructive Lung Disease (GOLD).
Global strategy for the diagnosis, management, and prevention of chronic obstructive pulmonary disease 2024 report. Global Initiative for Chronic Obstructive Lung Disease (GOLD). Accessed Apr. 16, 2024. https://goldcopd.org/2024-gold-report/.
Harries, TH et al., Blood eosinophil count, a marker of inhaled corticosteroid effectiveness in preventing COPD exacerbations in post-hoc RCT and observational studies: systematic review and meta-analysis. Respir Res. Jan. 3, 2020;21(1):3.
Houlihan, W.J. et al., Synthesis and proton-NMR spectra, Journal of Heterocyclic Chemistry, vol. 19, 6(1982):1453-6.
Hurst, JR et al., Prognostic risk factors for moderate-to-severe exacerbations in patients with chronic obstructive pulmonary disease: a systematic literature review. Respir Res. 2022;23(1):213.
Iheanacho, I. et al., Economic burden of chronic obstructive pulmonary disease (COPD): a systematic literature review. Int J Chron Obstruct Pulmon Dis. 2020;15:439-460.
Jansen, M., Derivatives of some nuclear methoxylated B-phenylethylamines, vol. 50, (1931):617-37.
Kew, KM et al., Inhaled steroids and risk of pneumonia for chronic obstructive pulmonary disease. Cochrane Database Syst. Rev. 2014; 2014(3):Cd010115.
Kienzle, F. et al., Synthesis of 6,7-dihydro-2H-pyrimido[6, 1-a]isoquinolin-4(3H)-ones and analogous compounds and their activity as blood platelet aggregation inhibitors, Helvetica Chimica Acta, vol. 69, 7(1986):1671-80.
Kijima, I, et al., Synthesis and reactivities of triisocyanatoantimony, Japan, Nippon Kagaku Kaishi, vol. 12, (1986):1754-57.
Lal, B. et al., Synthesis of 2-substituted-6,7-dihydro-4H-pyrimido[6, 1-a]thieno[2,3-c]- and [3,2-c]pyridin-4-ones, Heterocycles, vol. 24, 7(1986):1977-85.
Lal, B. et al., Trequinsin, a potent new antihypertensive vasodilator in the series of 2-(arylimino)-3-alkyl-9, 10-dimethoxy-3,4,6,7-tetrahydro-2H-pyrimido[6, 1-a]isoquinolin-4-ones, Journal of Medicinal Chemistry, vol. 27, 11(1984):1470-80.
Lipson, DA et al., Fulfil trial: once-daily triple therapy for patients with chronic obstructive pulmonary disease. Am J Respir Crit Care Med. 2017; 196(4):438-446.
Lipson, DA et al., Once-daily single-inhaler triple versus dual therapy in patients with COPD. N Engl J Med. 2018; 378(18):1671-1680.
Mahler, DA et al., Effect of ensifentrine on dyspnea in patients with moderate-to-severe chronic obstructive pulmonary disease: pooled analysis of the ENHANCE trials. Expert Rev Respir Med. Aug. 2024;18(8): 645-654. doi: 10.1080/17476348.2024.2389960. Epub Aug. 8, 2024. PMID: 39106052.
Mahler, DA et al., Ensifentrine, A Novel, Selective Inhibitor of PDE3 and PDE4, Improved Dyspnea in Subjects With Symptomatic, Moderate-to-Severe COPD Over 24 Weeks (Abstract and Poster), A27. Emerging Treatments and Therapeutic Strategies in COPD: Results of Clinical Trials and Observational Studies / Poster Discussion Session / Sunday May 19/09:15 AM / San Diego Convention Center, Room 33A-C. American Journal of Respiratory and Critical Care Medicine 2024;209:A1205.
Mannich, C. et al., Berichte der Deutschen Chemischen Gesellschaft, vol. 43, (1910):189-97.

(56) References Cited

OTHER PUBLICATIONS

Mannino, D et al., Treatment patterns for chronic obstructive pulmonary disease (COPD) in the United States: results from an observational cross-sectional physician and patient survey. Int J Chron Obstruct Pulmon Dis. 2022;17:749-761.
Martinez, FJ et al., Determinants of response to roflumilast in severe chronic obstructive pulmonary disease. Pooled analysis of two randomized trials. Am J Respir Crit Care Med. Nov. 15, 2018;198(10):1268-1278.
Maurer et al., "Late Breaking Abstract—RPL554, a first-in-class dual PDE3/4 inhibitor, causes significant bronchodilation and symptom relief; a Phase 2B COPD study," European Respiratory Journal, 2018, 52:OA1940, 1-5.
Milara, J et al., Oxidative stress-induced glucocorticoid resistance is prevented by dual PDE3/PDE4 inhibition in human alveolar macrophages. Clin Exp Allergy. 2011;41(4):535-46.
Miravitlles, M et al., A pooled analysis of mortality in patients with COPD receiving dual bronchodilation with and without additional inhaled corticosteroid. Int J Chron Obstruct Pulmon Dis. 2022;17:545-558.
Negewo et al., "Peripheral blood eosinophils: a surrogate marker for airway eosinophilia in stable COPD," International Journal of COPD, 2016, 11:1495-1504.
Nici, L et al., Pharmacologic management of chronic obstructive pulmonary disease. an official American Thoracic Society clinical practice guideline. Am J Respir Crit Care Med. 2020;201(9):e56-e69.
No Author, European Medicines Agency, Guideline on the sterilisation of the medicinal product, active substance, excipient and primary container, Apr. 11, 2016.
No Author, European Medicines Agency, Guideline on the sterilisation of the medicinal product, active substance, excipient and primary container, Mar. 6, 2019.
Pai, N.R. et al., Synthesis of novel analogs 3,4-dihydro-1H-quinolin-2-one derivatives as typical Antidepressant, Sedative and anti-Parkinson agents, Heterocyclic Letters, vol. 2, 1 (2012):117-128.
Pascoe, S et al., Blood eosinophils and treatment response with triple and dual combination therapy in chronic obstructive pulmonary disease: analysis of the IMPACT trial. Lancet Respir Med 2019;7:745-756.
Pasquale, MK et al., Impact of exacerbations on health care cost and resource utilization in chronic obstructive pulmonary disease patients with chronic bronchitis from a predominantly Medicare population. Int J Chron Obstruct Pulmon Dis. 2012; 7:757-64.
Pavord, ID et al., Blood eosinophil count and pneumonia risk in patients with chronic obstructive pulmonary disease: a patient-level meta-analysis. Lancet Respir Med. 2016;4(9):731-741.
Pfleiderer, V.W. et al., Synthesis of 9-substituted xanthines, Justus Liebigs Annalen der Chemie, vol. 631, (1960):168-74.
Rabe, KF et al., Anti-inflammatory effects of roflumilast in chronic obstructive pulmonary disease (ROBERT): a 16-week, randomised, placebo-controlled trial. Lancet Respir Med. Nov. 2018;6(11):827-836. doi: 10.1016/S2213-2600(18)30331-X. Epub Sep. 14, 2018. Erratum in: Lancet Respir Med. Oct. 12, 2018;: PMID: 30224319.
Rabe, KF et al., Triple inhaled therapy at two glucocorticoid doses in moderate-to-very-severe COPD. N Engl J Med. 2020; 383(1):35-48.
Ratel, M. et al., Imidazolium-Based Ionic Liquid Surfaces for Biosensing, Analytical Chemistry, vol. 85, 12 (2013):5770-5777.
Rothnie, KJ et al., Natural history of chronic obstructive pulmonary disease exacerbations in a general practice-based population with chronic obstructive pulmonary disease. Am J Respir Crit Care Med. 2018;198(4):464-471.
Schmidt, DT et al., The effect of selective and non-selective phosphodiesterase inhibitors on allergen- and leukotriene C(4)-induced contractions in passively sensitized human airways. Br J Pharmacol. 2000;131(8):1607-18.
Sciurba, F.C. et al., Ensifentrine, a novel dual phosphodiesterase (PDE) 3 and 4 inhibitor, improves lung function, symptoms, quality of life and reduces exacerbation rate and risk in patients with COPD: results from replicate phase 3 trials, Am J Respir Crit Care Med, (2023):207, poster.
Sciurba, FC et al., Dual Phosphodiesterase 3 and 4 Inhibitor Ensifentrine Reduces Exacerbation Rate and Risk in Patients With Moderate to Severe COPD. Chest. Aug. 27, 2024:S0012-3692(24)04937-7. doi: 10.1016/j.chest.2024.07.168. Epub ahead of print. PMID: 39197510.
Sciurba, FC et al., Ensifentrine, A Novel, Selective Inhibitor of PDE3 and PDE4, Reduced Moderate/Severe Exacerbation Rate and Risk in Subjects With COPD Regardless of Baseline Blood Eosinophils (Abstract and Poster), B52. Evidence for Therapeutic Strategies in COPD: From Established to Emerging/ Thematic Poster Session / Monday, May 20/09:15 AM-04:15 PM / San Diego Convention Center, Area F. American Journal of Respiratory and Critical Care Medicine 2024;209:A3820.
Singh et al., "Blood Eosinophil Counts in Chronic Obstructive Pulmonary Disease: A Biomarker of Inhaled Corticosteroid Effects," Tuberculosis and Respiratory Disease, 2020, 83:185-194.
Sonnex, K et al., Impact of smoking status on the efficacy of inhaled corticosteroids in chronic obstructive pulmonary disease: a systematic review. BMJ Open. 2020;10(4):e037509.
SPAN 20 (sorbitan monolaurate) Product Page, Sigma Aldrich, Published 2024 (Year: 2024), 8 pages.
Suissa, S, Number needed to treat in COPD: exacerbations versus pneumonias. Thorax. 2013;68(6):540-3.
Suissa, Samy, Single-inhaler triple versus dual bronchodilator therapy for Gold E and other exacerbating patients with COPD: Real-world comparative effectiveness and safety, European Respiratory Journal 2023.
Tashkin DP, et al., Concomitant inhaled corticosteroid use and the risk of pneumonia in COPD: a matched-subgroup post hoc analysis of the UPLIFT trial. Respir Res. 2018; 19(1):196.
Tran, P. et al., Structure-activity relationship of human glutaminyl cyclase inhibitors having an N-(5-methy-1H-imidazol-1-yl)propyl thiourea template, Bioorganic & Medicinal Chemistry, vol. 21, 13 (2013):3821-3830.
Turner, MJ et al., The dual phosphodiesterase 3 and 4 inhibitor RPL554 stimulates CFTR and ciliary beating in primary cultures of bronchial epithelia. Am J Physiol Lung Cell Mol Physiol. 2015;310(1):L59-70.
Tween 20 (polyoxyethylene sorbitan monolaurate) Product Page, Sigma Aldrich, Published 2024 (Year 2024), 9 pages.
USP 1229.8 Dry Heat Sterilization 2018.
Verona Pharma, Clinical Study Protocol, Version 5.0, Apr. 30, 2021 (Year: 2021).
Vogelmeier, CF et al., Evaluation of exacerbations and blood eosinophils in UK and US COPD populations. Respir Res. 2019;20(1):178.
Watz, H et al., Symptom improvement following treatment with the inhaled dual phosphodiesterase 3 and 4 inhibitor ensifentrine in patients with moderate to severe COPD—A Detailed Analysis. Int J Chron Obstruct Pulmon Dis. 2020;15:2199-2206.
Zafari, Z. et al., Projecting long-term health and economic burden of COPD in the United States. Chest. 2021; 159(4):1400-1410.
Zafari, Z. et al., The projected economic and health burden of sub-optimal asthma control in Canada. Respiratory Medicine. 2018; 138:7-12.
Agusti et al., Global Initiative for chronic Obstructive Lung Disease 2023 Report: GOLD Executive Summary, European Respiratory Journal Task Force Report, 2023, 61:2300239, 1-26.
Anoro Ellipta Prescribing Information, 2013, revised Jun. 2023, 37 pages.
Bateman et al., Aclidinium bromide and formoterol fumarate as a fixed-dose combination in COPD: pooled analysis of symptoms and exacerbations from two six-month, multicentre, randomised studies (ACLIFORM and AUGMENT), Respiratory Research, 2015, 16(1):92, 1-13.
Bevespi Aerosphere Prescribing Information, 2016, revised Mar. 2023, 12 pages.
Boswell-Smith et al., "The Pharmacology of Two Novel Long-Acting Phosphodiesterase 3/4 Inhibitors, RPL554 [9, 10-Dimethoxy-2(2,4,6-trimethylphenylimino)-3-(N-carbamoyl-2-aminoethyl)-3,4,6,7-

(56) References Cited

OTHER PUBLICATIONS tetrahydro-2H-pyrimido[6, 1-a]isoquinolin-4-one] and RPL565 (6,7-Dihydro-2-(2,6-diisopropylphenoxy)-9, 10-dimethoxy-4H-pyrimidi]6, 1-a]isoquinolin-4-one]," The Journal of Pharmacology and Experimental Therapeutics, 2006, 318:840-848.

Breztri Aerosphere Prescribing Information, 2020, revised Jul. 2020, 19 pages.

Calzetta et al., "Pharmacological characterization of the interaction between the dual phosphodiesterase (PDE) 3/4 inhibitor RPL554 and glycopyrronium on human isolated bronchi and small airways," Pulmonary Pharmacology & Therapeutics, 2015, 32:15-23.

Cortijo et al., "Roflumilast a phosphodiesterase 4 inhibitor, alleviates bleomycin-induced lung injury," British Journal of Pharmacology, 2009, 156:534-544.

De la Loge et al., Relationship Between FEV1 and Patient-Reported Outcomes Changes: Results of a Meta-Analysis of Randomized Trials in Stable COPD, Chronic Obstr. Pulm. Dis., Mar. 15, 2016, 3(2):519-538.

Donohue, James F., Minimal clinically important differences in COPD lung function, Chronic Obstr. Pulm. Dis., Mar. 2005, 2(1):111-124.

Duaklir Pressair Prescribing Information, 2019, revised Mar. 2019, 33 pages.

E-RS (EXACT—Respiratory Symptoms), User Manual (Version 3.0), Oct. 2014, 26 pages.

Eneje et al., A Single Dose of a Novel Nebulised PDE3/4 Inhibitor RPL554 Increased FEV1 in Patients with Cystic Fibrosis and Demonstrated a Reproducible Pharmacokinetic Profile, Pediatric Pulmonology, 2018, 53(Suppl. S2)S228, Abstract 215, 1 page.

Ferguson et al. Triple therapy with budesonide/glycopyrrolate/formoterol fumarate with co-suspension delivery technology versus dual therapies in chronic obstructive pulmonary disease (KRONOS): a double-blind, parallel-group, multicentre, phase 3 randomised controlled trial, Lancet Respir, Med., 2018, 6:747-758.

Gauldie et al., "Adenovirus-Vector-Mediated Cytokine Gene Transfer to Lung Tissue," Annals New York Academy of Sciences, 1996, 796:235-244.

Herrmann et al., "BI 1015550 is a PDE4B Inhibitor and a Clinical Drug Candidate for the Oral Treatment of Idiopathic Pulmonary Fibrosis," Frontiers in Pharmacology, Apr. 20, 2022, 13:838449, 1-17.

Johnson, D.L., "The Effect of Phosphate Buffer on Aerosol Size Distribution of Nebulized Bacillus subtilis and *Pseudomonas fluorescens* Bacteria," Aerosol Science and Technology, 1999, 30:202-210.

Jones et al., Minimally Clinically Important Differences in Pharmacological Trials, American Journal of Respiratory and Critical Care Medicine, Feb. 1, 2014, 189(3):250-255.

Jones, Paul W., St. George's Respiratory Questionnaire: MCID, Chronic Obstr. Pulm. Dis., 2005, 2(1):75-79.

Kolb et al., "Differences in the Fibrogenic Response after Transfer of Active Transforming Growth Factir-beta1 Gene to Lungs of 'Fibrosis-prone' and 'Fibrosis-resistant' Mouse Strains," Am. J. Respir. Cell Mol. Biol., 2002, 27:141-150.

Kumar et al., "Basic Concepts of Sterilization Techniques," Research Journal of Pharmacology and Pharmacodynamics, Oct.-Dec. 2021, 13(4):155-161.

Lonhala Magnair Prescribing Information, 1961, revised Dec. 2017, 64 pages.

Mahler et al., The MCID of the Transition Dyspnea Index is a Total Score of One Unit, Chronic Obstr. Pulm. Dis., 2005, 2(1):99-103.

Maier et al., "Inhibition of phosphodiesterase 4 (PDE4) reduces dermal fibrosis by interfering with the release of interleukin-6 from M2 macrophages," Ann. Rheum. Dis., 2017, 76:1133-1141.

Matsuhira et al., "A novel phosphodiesterase 4 inhibitor, AA6216, reduces macrophage activity and fibrosis in the lung," European Journal of Pharmacology, Aug. 25, 2020, 885:173508, 1-7.

Miravitlles M et al., Pharmacological strategies to reduce exacerbation risk in COPD: a narrative review, Respiratory Research, 2016, 17(1):112, 1-15.

Murray et al., "Hyperresponsiveness of IPF/UIP fibroblasts interplay between TGFbeta1, IL-13 and CCL2," Int. J. Biochem. Cell Biol., Feb. 23, 2008, 40:2174-2182.

Newman et al., Low Oral Bioavailability of RPL554, a First-in-Class Dual PDE3/4 Inhibitor, Demonstrates that Its Nebulized, Inhaled Formulation Is Appropriate for Delivering Optimal Pulmonary Dose, Am. J. Respir. Crit. Care Med., 2018; 197:A3022, Abstract, 3 pages.

Ogawa et al., "Macrophages in lung fibrosis," International Immunology, Jul. 16, 2021, 33(12):665-671.

Rheault et al., The effect of fluconazole on the pharmacokinetics of ensifentrine in healthy individuals, European Respiratory Journal, 2021; 58:(Suppl. 65):PA2137, Abstract, 4 pages.

Richeldi et al., "Trial of a Preferential Phosphodiesterase 4B Inhibitor for Idiopathic Pulmonary Fibrosis," The New England Journal of Medicine, May 15, 2022, 386:2178-2187.

Rickard et al., The Dual Phosphodiesterase (PDE) 3 and 4 Inhibitor Ensifentrine Does Not Prolong QT Interval in Healthy Volunteers, Am. J. Respir. Crit. Care Med., 2022, 205:A5605, Abstract, 1 page.

Sime et al., "Adenovector-mediated gene transfer of active transforming growth factor-beta1 induces prolonged severe fibrosis in rat lung," J. Clin. Invest., 1997, 100(4):768-776.

Singh et al., "The short term bronchodilator effects of the dual PDE3 and PDE4 inhibitor RPL554 in COPD," European Respiratory Journal, 2018; in press (https://doi.org/10.1183/13993003.01074-2018), 33 pages.

Singh et al., A Phase I, Randomised, Double Blind, Placebo Controlled, Study to Assess the Safety, Tolerability and Pharmacokinetics of Multiple Inhaled Doses of RPL554 Administered by Nebuliser to Healthy Male Subjects and Stable COPD Patients, Am. J. Respir. Crit. Care Med., 2016, 193:A6838, Abstract, 3 pages.

Singh et al., A Phase I, Randomised, Double Blind, Placebo Controlled, Study to Assess the Safety, Tolerability and Pharmacokinetics of Single Inhaled Doses of the Dual Phosphodiesterase 3/4 (PDE3/4) Inhibitor RPL554 Administered by Nebuliser to Healthy Male Subjects, Am. J. Respir. Crit. Care Med., 2016, 193:A6839, Abstract, 3 pages.

Stiolto Respimat Prescribing Information, 2015, revised Jan. 2025, 21 pages.

Striverdi Respimat Medical Review, Center for Drug Evaluation and Research, NDA 203108, 2012, 385 pages.

Striverdi Respimat Prescribing Information, 2014, revised Jan. 2025, 18 pages.

Symbicort Prescribing Information, 2006, revised Feb. 2009, 73 pages.

Trujillo et al., Decrease in exacerbations during the coronavirus disease 2019 pandemic in a cohort of veterans with COPD, Chronic Obstr. Pulm. Dis., 2021, 8(4): 572-579.

Utibron Neohaler Prescribing Information, 2015, revised May 2019, 28 pages.

Verona Pharma, Clinical Study Protocol, Version 1.0, May 28, 2018, 66 pages.

Wells et al., "Pulmonary fibrosis: 'idiopathic' is not 'cryptogenic'", Eur. Respir. J., 2019, 53:1900400, 1-3.

Woodcock et al., "Reducing lung function decline in patients with idiopathic pulmonary fibrosis: potential of nintedanib," Drug Design, Development and Therapy, 2013, 7:503-510.

ClinicalTrials.gov, "A Phase 3 Clinical Trial to Evaluate the Safety and Efficacy of Ensifentrine in Patients with COPD," ID NCT04535986, Verona Pharma plc, Nov. 13, 2023, 28 pages.

European Medicines Agency (EMEA), "Guideline on the Evaluation of the Pharmacokinetics of Medicinal Products in Patients with Decreased Renal Function," Dec. 17, 2015, 15 pages.

European Medicines Agency (EMEA), "Guideline on the Evaluation of the Pharmacokinetics of Medicinal Products in Patients with Impaired Hepatic Function," Feb. 17, 2005, 10 pages.

International Search Report and Written Opinion dated May 14, 2025 in PCT/EP2025/053115.

Singh et al. "Blood Eosinophil Counts in Clinical Trials for Chronic Obstructive Pulmonary Disease," American Journal of Respiratory and Critical Care Medicine, Sep. 1, 2020, 202(5):660-671.

(56) References Cited

OTHER PUBLICATIONS

Overview of Pharmaceutical Impurity: Introduction, Agilent Technologies Japan, Ltd., Apr. 20, 2018, pp. 1-40, with English translation , 83 total pages.

* cited by examiner

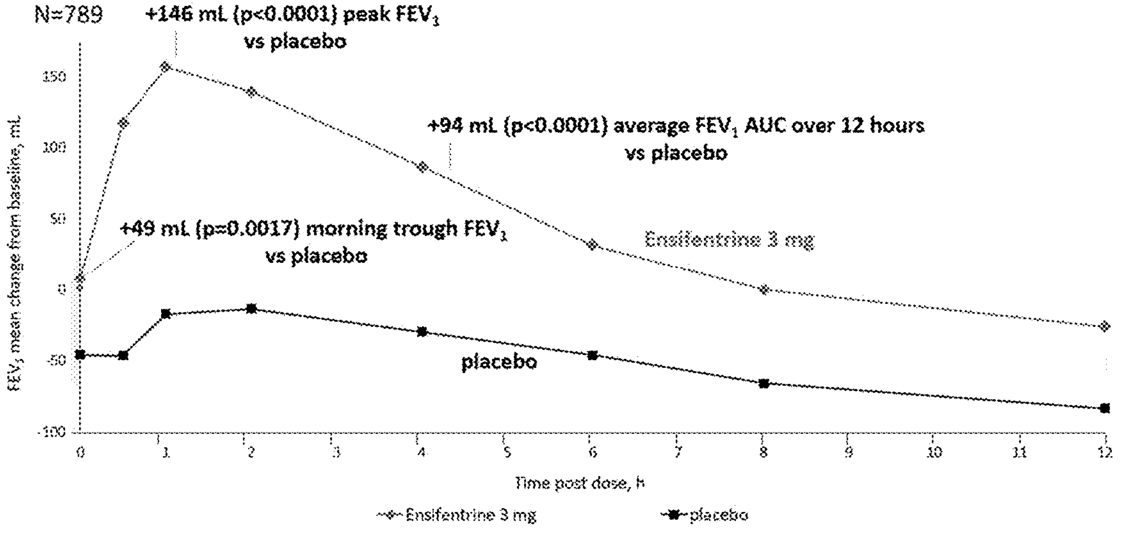
N=789
+146 mL (p<0.0001) peak $FEV_1$ vs placebo
+94 mL (p<0.0001) average $FEV_1$ AUC over 12 hours vs placebo
+49 mL (p=0.0017) morning trough $FEV_1$ vs placebo
Ensifentrine 3 mg
placebo
$FEV_1$, mean change from baseline, mL
150
100
50
0
-50
-100
0
1
2
3
4
5
6
7
8
9
10
11
12
Time post dose, h
Ensifentrine 3 mg
placebo

ENSIFENTRINE FOR DECREASING THE FREQUENCY/SEVERITY OF COPD EXACERBATIONS

CROSS REFERENCE

This application is a bypass continuation of International Application No. PCT/GB2023/052084, filed on Aug. 7, 2023, which claims priority to U.S. Provisional Application No. 63/502,977, filed on May 18, 2023, U.S. Provisional Application No. 63/370,699, filed on Aug. 8, 2022, U.S. Provisional Application No. 63/370,696, filed on Aug. 8, 2022, and U.S. Provisional Application No. 63/370,694, filed on Aug. 8, 2022, each of which is incorporated herein by reference in its entirety.

FIELD OF THE INVENTION

The present invention relates to decreasing the frequency and/or severity of chronic obstructive pulmonary disease (COPD) exacerbations in a patient suffering from COPD. The present invention also relates to the treatment of COPD in patients susceptible to COPD exacerbations.

BACKGROUND OF THE INVENTION

Ensifentrine (N-(2-{(2E)-9,10-dimethoxy-4-oxo-2-[(2,4,6-trimethylphenyl)imino]-6,7-dihydro-2H-pyrimido[6,1-a]isoquinolin-3 (4H)-yl} ethyl) urea: also known as RPL554) is a dual PDE3/PDE4 inhibitor and is described in WO 00/58308 A1.

As a combined PDE3/PDE4 inhibitor, ensifentrine has both bronchodilatory and anti-inflammatory activity and is useful in the treatment of respiratory disorders including chronic obstructive pulmonary disease (COPD). The chemical structure of ensifentrine is shown below.

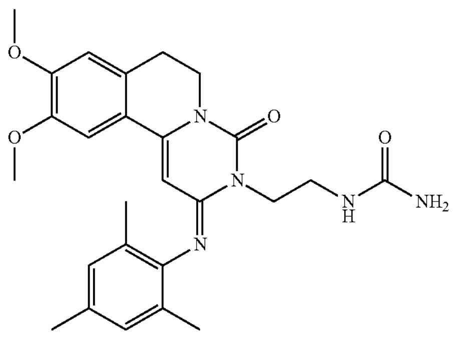 [SMILES: COc1cc2c(cc1OC)-c1c/c(=N\c3c(C)cc(C)cc3C)n(CCNC(N)=O)c(=O)n1CC2]

COPD is a progressive, long-term condition affecting a large number of people worldwide. Ongoing symptoms include breathlessness and cough. However, many COPD patients also suffer from occasional, temporary worsening of their symptoms (known as a COPD exacerbation). A COPD exacerbation typically involves an increase in breathlessness (dyspnea), the presence of excessive mucus (increased sputum volume), change in mucus colour (sputum purulence) and/or an increase in coughing.

Certain patient groups are particularly susceptible to COPD exacerbations. This includes patients suffering from additional respiratory conditions such as asthma and patients suffering from allergic conditions. Patients susceptible to COPD exacerbations have typically experienced COPD exacerbations previously.

COPD exacerbations can be severe and can limit the quality of life of COPD patients. Not all drugs which are disclosed for use in treating COPD are equally effective in reducing the severity and/or frequency of COPD exacerbations or time to first COPD exacerbation. It would therefore be advantageous for a COPD drug to be used which is particularly effective in reducing the severity and/or frequency of COPD exacerbations when there is a specific clinical need to address such exacerbations.

SUMMARY OF THE INVENTION

It is a surprising finding of the present invention that ensifentrine is highly effective in reducing the frequency and/or severity of COPD exacerbations in COPD patients. In particular, ensifentrine has been found to lead to a more pronounced reduction in COPD exacerbations compared to many known treatments for COPD.

The invention accordingly provides a compound for use in a method for decreasing the frequency and/or severity of chronic obstructive pulmonary disease (COPD) exacerbations in a patient suffering from COPD, wherein the compound is ensifentrine or a pharmaceutically acceptable salt thereof. The invention also provides a compound for use in a method for increasing the time to first COPD exacerbation in a patient suffering from COPD, wherein the compound is ensifentrine or a pharmaceutically acceptable salt thereof.

Also provided by the invention is a compound for use in a method for treating chronic obstructive pulmonary disease (COPD) in a patient, wherein: the compound is ensifentrine or a pharmaceutically acceptable salt thereof; and the patient is susceptible to COPD exacerbations.

The invention also provides a method for decreasing the frequency and/or severity of chronic obstructive pulmonary disease (COPD) exacerbations in a patient suffering from COPD, the method comprising administering a therapeutically effective amount of a compound to the patient, which compound is ensifentrine or a pharmaceutically acceptable salt thereof.

The invention further provides a method of treating COPD in a patient, which method comprises administering a therapeutically effective amount of a compound which is ensifentrine or a pharmaceutically acceptable salt thereof to the patient, wherein the patient is susceptible to COPD exacerbations.

Further provided by the invention is use of a compound in the manufacture of a medicament for use in a method for decreasing the frequency and/or severity of chronic obstructive pulmonary disease (COPD) exacerbations in a patient suffering from COPD, wherein the compound is ensifentrine or a pharmaceutically acceptable salt thereof.

Also provided by the invention is use of a compound which is ensifentrine or a pharmaceutically acceptable salt thereof in the manufacture of a medicament for treating COPD, wherein the patient is susceptible to COPD exacerbations.

BRIEF DESCRIPTION OF THE FIGURES

FIG. 1 shows the $FEV_1$ profile over 12 hours at Week 12.

DETAILED DESCRIPTION OF THE INVENTION

The compound decreases the frequency and/or severity of chronic obstructive pulmonary disease (COPD) exacerbations in a patient suffering from COPD. The compound may decrease the frequency of COPD exacerbations. For instance, the patient may suffer two or fewer (for instance one or zero) COPD exacerbations per year while being treated with the compound, for instance as a maintenance therapy. The number of COPD exacerbations experienced by the patient per year during treatment with the compound may be one to three fewer than the number of COPD exacerbations experienced by the patient per year prior to treatment with the compound.

The compound may increase the time to a first COPD exacerbation in the patient. Accordingly, the patient may not have yet experienced a COPD exacerbation and the compound may increase the time until the patient experiences a first COPD exacerbation (i.e. the first COPD exacerbation is delayed). The compound may accordingly reduce the risk of COPD exacerbations in a COPD patient.

The COPD exacerbations typically comprise one or more of dyspnea (breathlessness), increased coughing, increased sputum volume, sputum purulence, wheezing, sore throat, a cold, and fever. Sputum purulence is a change in the colour of spontaneously expectorated samples from uncoloured to yellow-green. The COPD exacerbation may last for at least one day or at least two days.

A COPD exacerbation may comprise (A) worsening of two or more of the following major symptoms for at least two consecutive days: dyspnea, sputum volume and sputum purulence or (B) worsening of any one major symptom together with any one of the following minor symptoms for at least two consecutive days: sore throat, colds (nasal discharge and/or nasal congestion), fever (oral temperature>37.5° C.) without other cause and increased cough. For instance, a COPD exacerbation may comprise worsening of two or more of the major symptoms (dyspnea, sputum volume and sputum purulence) for at least two consecutive days.

A COPD exacerbation may be a moderate COPD exacerbation or a severe COPD exacerbation. A moderate exacerbation is defined as worsening symptoms of COPD (as defined above) requiring a minimum of three days of treatment with oral/systemic corticosteroids and/or antibiotics. A severe exacerbation is defined as worsening symptoms of COPD (as defined above) requiring in-patient hospitalization. The compound may reduce the severity of COPD exacerbations in a patient, and accordingly the compound may be for use in preventing severe COPD exacerbations in a patient. For instance, the patient may experience no severe COPD exacerbations in the year following first administration of the compound.

The compound may lengthen the time to a COPD exacerbation. For instance, it may increase the time to an exacerbation by two or more months.

The patient is typically susceptible to COPD exacerbations. Typically, a "patient susceptible to COPD exacerbations" is a patient suffering from one or more co-morbidities (other than COPD). Said patient is typically suffering from one or more disease or condition selected from asthma, pulmonary hypertension, bronchiectasis, allergy, lung cancer, chest infection, cystic fibrosis, pulmonary fibrosis, pneumonia, hay fever, allergic rhinitis, bronchitis, emphysema, adult respiratory distress syndrome (ARDS), interstitial lung disease or tuberculosis, optionally wherein the asthma is allergic asthma, steroid resistant asthma, severe asthma or paediatric asthma. The patient susceptible to COPD exacerbation may have a chronic bronchitis etiology, may have impaired lung function (such as 30 to 70% predicted $FEV_1$) or may have COPD symptoms despite use of long-acting muscarinic receptor antagonist (LAMA) or a long-acting beta-adrenergic receptor agonist (LABA) therapy.

For instance, the compound may be for use in treating COPD in a patient suffering from both COPD and asthma. The compound may be for use in treating COPD a patient suffering from both COPD and pulmonary hypertension. The compound may be for use in treating COPD in a patient suffering from both COPD and bronchiectasis.

Other risk factors for COPD exacerbation include: high serum immunoglobulin (lg), previous tuberculosis, severe airflow obstruction, chest infection and one or more hospital admission for COPD exacerbations in the previous year.

In some cases, the patient has suffered one or more COPD exacerbations in the year preceding first administration of the compound. For instance, the patient may have suffered two or more COPD exacerbations in the year preceding first administration of the compound. The patient may for instance have suffered from at least one severe COPD exacerbation (i.e. requiring hospital treatment) in the preceding year. The patient may have suffered one or more COPD exacerbations in the six months preceding first administration of the compound, or one or more COPD exacerbations in the one month preceding first administration of the compound.

The patient may be male. The patient may be female. The patient may have an age of greater than or equal to 65 years. The patient may have an age of less than 65 years. The patient may be taking a background medication selected from one or more of a long-acting muscarinic antagonist (LAMA), a long-acting beta-agonist (LABA) and an inhaled corticosteroid (ICS).

The compound is ensifentrine or a pharmaceutically acceptable salt thereof. Pharmaceutically acceptable salts are well known to the skilled person. Typically, the compound is ensifentrine (i.e. ensifentrine free base).

The method typically comprises administering the compound to the patient by inhalation. A pharmaceutical composition comprising the compound and one or more pharmaceutically acceptable excipients or diluents is typically administered to the patient by inhalation, for instance by nebuliser, pressurised metered dose inhaler (pMDI) or dry powder inhaler (DPI).

Preferably, the method comprises administering the compound to the patient by inhalation from a nebuliser. Nebulisers aerosolise a liquid pharmaceutical composition into an aerosol that is inhaled into a patient's respiratory tract. Examples of nebulisers include a soft mist nebuliser, a vibrating mesh nebuliser, a jet nebuliser and an ultrasonic wave nebuliser. Suitable nebuliser devices include the Philips I-neb™ (Philips), the Philips SideStream (Philips), the AeroNeb® (Philips), the Philips InnoSpire Go (Philips), the Pari LC Sprint (Pari GmbH), the AERxR™ Pulmonary Delivery System (Aradigm Corp) and the Pari LC Plus Reusable Nebuliser (Pari GmbH). The nebulizer may for instance be a PARI LC Sprint jet nebulizer with a PARI Vios® PRO Aerosol Delivery System PARI BOY® compressor. The compound may be inhaled via the nebuliser for from 1 to 15 minutes.

Typically, the method comprises administering the compound to the patient once, twice or three times per day, for instance twice or three times per day. The compound may be administered to the patient by inhalation once, twice or three times a day. Preferably the method comprises administering the compound to the patient by inhalation twice a day. The method may comprise administering a first dose of the compound in the morning (for instance within 3 hours following waking) and a second dose of the compound in the evening (for instance within 3 hours before bed). Typically, the morning and evening doses are administered from 10 to 14 hours apart, for instance about 12 hours apart.

The compound may be used in any suitable therapeutically effective amount. Typically, the daily dose of the compound is from 0.1 to 20 mg. Typically, the method comprises administering a total daily dose of the compound of from 0.5 to 10 mg. Preferably, the total daily dose of the compound (e.g. ensifentrine free base) is from 5 to 7 mg, for instance about 6 mg per day. As used herein, the term "about" may represent a variation of ±10% of the stated value. The total daily dose of the compound may be 6.0 mg. Typically, the compound is administered twice a day in two separate doses which are the same or similar. For instance, the method may comprise administering the compound to the patient twice a day in a first dose of from 1 to 5 mg and a second dose of from 1 to 5 mg. Typically, the method may comprise administering the compound to the patient twice a day in a first dose of from 2 to 4 mg and a second dose of from 2 to 4 mg.

Preferably, the method comprises administering two doses of about 3 mg ensifentrine free base to the patient per day by inhalation. The method preferably comprises administering a dose of about 3 mg of the compound to the patient twice a day (3 mg BID) by inhalation. More preferably, the method comprises administering by nebuliser a dose of about 3 mg the compound to the patient twice a day. Each dose may be 3.0 mg free base ensifentrine administered by nebulizer.

The compound is typically used as a maintenance therapy. Typically, the method comprises administering the compound to the patient at least once per day for at least 8 weeks. The compound may be administered to the patient at least once per day for at least 16 weeks, preferably for at least 24 weeks. The compound may be administered daily to the patient for at least 1 year. The method may comprise administering the compound to the patient at least once every 24 hours, preferably at least twice every 24 hours, for at least 8 weeks, preferably for at least 16 weeks, more preferably for at least 24 weeks.

The compound is preferably administered as a suspension formulation, i.e. a suspension of particles comprising the compound in a diluent. The compound may alternatively be delivered as a dry powder, for instance a dry powder comprising particles comprising the compound and particles of a carrier such as lactose.

The method typically comprises administering an inhalable pharmaceutical composition comprising a suspension of particles of the compound in a diluent. The particles comprising the compound typically have a particle size distribution with a Dv50 of from 0.5 μm to 5.0 μm. The particles preferably have a Dv50 of from 1.0 μm to 2.0 μm.

Particle sizes are described herein by reference to the Dv50 value, which is the median particle size for a volume distribution. Thus, half the volume of the particles have diameters of less than the Dv50 value and half the volume of the particles have diameters of greater than the Dv50 value. This is a well-known manner in which to describe particle size distributions.

The technique used to measure the Dv50 values as stated herein is typically laser diffraction. The particle size distribution of the particles comprising the compound may be as measured by laser diffraction using a wet powder dispersion system. For instance, the particle size distribution can be measured by laser diffraction using a Malvern Spraytec in conjunction with a wet dispersion cell. Typically, the instrument parameters for the Malvern Spraytec are as follows:

particle—standard opaque particle:
refractive index Particle—1.50;
refractive index (imaginary)—0.50;
density of particle—1.00;
refractive index of dispersant—1.33:
controller unit—1000 RPM:
measurement type—timed:
initial sampling time—30s:
obscuration—20%-30%:
dispersant—1% Polysorbate 20 in deionised water.

The particles comprising the compound typically comprise ensifentrine (i.e. ensifentrine free base). The particles may comprise at least 90 wt % ensifentrine free base relative to the total weight of the particles. The particles may comprise at least 99 wt % ensifentrine. The particles may consist of ensifentrine.

The concentration of particles comprising the compound in the inhalable pharmaceutical composition is typically from 0.1 to 5.0 mg/mL, preferably from 0.1 to 2.5 mg/mL, more preferably from 1.0 to 2.0 mg/mL.

The inhalable pharmaceutical composition typically further comprises one or more tonicity adjusters, one or more buffers and one or more surfactants. The tonicity adjuster is typically sodium chloride.

Examples of buffers include a citrate buffer, a phosphate buffer, an acetate buffer, and a bicarbonate buffer. Preferably, the buffer is a phosphate buffer, for instance sodium dihydrogen phosphate dihydrate and/or disodium phosphate dihydrate.

Examples of surfactants include lecithin, oleic acid, polyoxyethylene glycol alkyl ethers (for instance PEG 300, PEG 600, PEG 1000, Brij 30, Brij 35, Brij 56, Brij 76 and Brij 97), polypropylene glycol (for instance PPG 2000), glucoside alkyl ethers, polyoxyethylene glycol octylphenol ethers, polyoxyethylene glycol alkylphenol ethers, glycerol alkyl esters, polyoxyethylene glycol sorbitan alkyl esters (polysorbates, for instance polysorbate 20, polysorbate 40, polysorbate 60 and polysorbate 80), sorbitan alkyl esters (for instance sorbitan monolaurate (Span 20), sorbitan monooleate (Span 80) and sorbitan trioleate (Span 85)), cocamide MEA, cocamide DEA, dodecyldimethylamine oxide, block copolymers of polyethylene glycol and polypropylene glycol (poloxamers), block copolymers of polyethylene glycol and polypropylene oxide (for instance Pluronic surfactants), polyvinyl pyrrolidone K25, polyvinyl alcohol, oligolactic acid, sodium dioctyl sulfosuccinate and polyethoxylated tallow amine (POEA).

Preferably, the one or more surfactants comprise a polysorbate and/or a sorbitan alkyl ester. The one or more surfactants may for instance comprise polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate) or polysorbate 80 (polyoxyethylene (20) sorbitan monooleate). The one or more surfactants may for instance comprise sorbitan monolaurate (Span 20), sorbitan monooleate (Span 80) or sorbitan trioleate (Span 85). Preferably, the sterile liquid vehicle comprises polysorbate 20 and/or sorbitan monolaurate (Span 20).

For instance, the method may comprise administering to the patient an inhalable liquid pharmaceutical composition comprising:

water;
particles consisting of ensifentrine free base at a concentration of from 0.1 to 20 mg/mL;

one or more tonicity adjusters at a total concentration of from 1.0 to 15 mg/mL;

one or more buffers at a total concentration of from 0.1 to 4 mg/mL; and one or more surfactants at a total concentration of from 0.05 to 3 mg/mL.

The inhalable liquid pharmaceutical composition may comprise:

water;

particles consisting of ensifentrine free base at a concentration of from 0.5 to 6 mg/mL;

sodium chloride at a concentration of from 5 to 12 mg/mL;

sodium dihydrogen phosphate dihydrate at a concentration of from 0.3 to 2 mg/mL;

disodium phosphate dihydrate at a concentration of from 0.3 to 2 mg/ml;

polysorbate 20 at a concentration of from 0.1 to 1.5 mg/mL; and sorbitan monolaurate at a concentration of from 0.01 to 0.5 mg/mL.

The compound may be used in combination with a second active agent. The compound may be administered separately or simultaneously with the second active agent. The patient may already be taking a second active agent as a background therapy for COPD. Alternatively, treatment with the second active agent may start at around the same time as treatment with the compound. The compound and the second active agent may be administered in a fixed combination.

The second active agent is typically a muscarinic receptor antagonist, a beta-adrenergic receptor agonist or an inhaled corticosteroid. The compound may accordingly be used in combination with muscarinic receptor antagonist, a beta-adrenergic receptor agonist or an inhaled corticosteroid. The second active agent may be a long-acting muscarinic receptor antagonist (LAMA) or a long-acting beta-adrenergic receptor agonist (LABA).

Examples of LAMAs include aclidinium, darotropium, tiotropium, glycopyrrolate and umeclidinium. Examples of LABAs include salmeterol, formoterol, indacaterol, vilanterol, olodaterol, abediterol and carmoterol. Examples of inhaled corticosteroids include beclomethosone, budesonide, fluticasone propionate, ciclesonide, mometasone and fluticasone furoate.

The patient may be using a beta-agonist (for instance salbutamol) as a rescue medication.

The invention is described in more detail by the following Example.

EXAMPLES

Study Design

A clinical study was conducted to determine the efficacy of ensifentrine in treating COPD compared with placebo. Ensifentrine was administered by nebuliser at a dose of 3 mg twice daily (BID) for 24 weeks. The study was a multi-centre, randomized, double-blind, parallel-group, placebo-controlled trial with around 800 patients and 5:3 randomization.

The study population included patients aged 40-80 years with moderate to severe COPD ($FEV_1$ 30%-70% p.n., $FEV_1$/forced vital capacity [FVC] ratio<0.7, with mMRC≥2). The randomization stratified (a) the use of stable background maintenance *LAMA* or LABA therapy use (approx. 50%. yes or no) and (b) cigarette smoking (current or former). Inhaled corticosteroid (ICS) maintenance therapy was permitted in up to 20% of patients under certain provisions.

The primary endpoint of the study was change from baseline in average $FEV_1$ area under the curve (AUC)0-12 h post-dose at week 12. Secondary endpoints of the study included: peak $FEV_1$ over 4 hours post-dose at Week 12: morning trough $FEV_1$ at Week 12; and other endpoints including moderate/severe COPD exacerbations frequency and time to first moderate or severe COPD exacerbation over 24 Weeks.

Methods

COPD severity is derived as follows: mild: 80%<=$FEV_1$, moderate: 50%<=$FEV_1$<80% predicted, severe: 30%<=$FEV_1$<50% predicted and very severe: $FEV_1$<30% predicted, post bronchodilator dose at Screening.

Baseline $FEV_1$ is the mean of the two measurements taken before study medication on the day of first dosing, i.e. ≤40 minutes and just prior to dosing, pre-dose on day 1.

Average $FEV_1$ AUCO-12 h is defined as area under the curve over 12 hours of the $FEV_1$, divided by 12 hours.

Exacerbations were defined as worsening of 2 or more major symptoms (dyspnea, sputum volume, and sputum purulence) or worsening of any 1 major symptom together with any 1 of the following minor symptoms: sore throat, colds, fever without other cause, and increased cough or wheeze for at least 2 consecutive days. COPD exacerbations were considered to be of moderate severity if treatment with systemic corticosteroids and/or antibiotics was required and were considered to be severe if hospitalization was required.

Formulation

The investigational product and placebo were provided in 2.5 mL unit dose format in an ampule and administered via a nebuliser. The formulation of the investigational product (ensifentrine suspension formulation) and placebo are shown in Table 1 below.

TABLE 1

| Constituent | Concentration (mg/mL) |
|---|---|
| Ensifentrine particles (RPL554) | 1.2 (for the active) or 0 (for Placebo) |
| Polysorbate 20 (Tween 20) | 0.50 |
| Sorbitan Monolaurate (Span 20) | 0.05 |
| Sodium Dihydrogen Phosphate Dihydrate | 0.744 |
| Disodium Hydrogen Phosphate Dihydrate | 0.853 |
| Sodium Chloride | 8.60 |
| Water | q.s. to 1 mL |

Results

The primary endpoint of average $FEV_1$ (AUC) 0-12 h at Week 12 was met. All subgroups showed improvement in lung function with ensifentrine that was statistically significant. The results are shown in Table 2 and FIG. 1.

TABLE 2

| Average $FEV_1$ (AUC)0-12 h post-dose at Week 12: Change from Baseline (CFB) | Ensifentrine 3 mg (n = 498) | Placebo (n = 291) |
|---|---|---|
| Observed N | 424 | 231 |
| Mean Baseline $FEV_1$, L | 1.3323 | 1.2316 |
| CFB Least Squares Mean, mL (95% CI) | 48.2 (30.0, 66.5) | −45.7 (−69.7, −21.6) |
| Placebo-corrected CFB LS Mean Diff., mL (95% CI) | 93.9 (64.5, 123.3) | — |
| p-value | <0.0001 | — |

Ensifentrine treatment resulted in approximately 40% reduction in relative risk of moderate or severe COPD exacerbation vs placebo (including 52% of patients on background bronchodilator medications).

Comparison with Other Drugs

As a comparison, the reduction in the rate of COPD exacerbations achieved with other treatments (long-acting muscarinic antagonists (LAMAs), long-acting beta-agonist (LABAs), inhaled corticosteroids (ICSs) and PDE4 inhibitors) taken from the literature is shown in Table 4 below.

TABLE 4

| Drug | Class | Population | Rate Ratio | Rate Reduction (=1-Rate Ratio) |
|---|---|---|---|---|
| Spiriva | LAMA | $FEV_1$ ≤60% predicted | 0.78 vs placebo | 22% |
| Tudorza | LAMA | 60% had at least one prior moderate or severe COPD exacerbation within the past year | 0.83 vs placebo | 17% |
| Breo 100/25 | LABA/ICS | at least one prior moderate or severe COPD exacerbation within the past year | 0.79 vs vilanterol | 21% |
| | | | 0.66 vs vilanterol | 34% |
| Symbicort | LABA/ICS | at least one prior moderate or severe COPD exacerbation within the past year | 0.74 vs formoterol | 26% |
| | | | 0.65 vs formoterol | 35% |
| Daliresp | PDE4 | At least one exacerbation in past year; LABA (44%) and LAMA (35%) use allowed | 0.85 vs placebo | 15% |
| | | | 0.82 vs placebo | 18% |
| Tanimilast | PDE4 | at least one prior moderate or severe COPD exacerbation within the past year | Not reported | 13-28% all doses vs placebo |

Ensifentrine was found to cause a greater reduction in the frequency of COPD exacerbations than other treatments.

CONCLUSION

It has been found that ensifentrine provides a statistically significant improvement in lung function in all subgroups of COPD patients in the study. In addition, ensifentrine has been found to be particularly effective in increasing the time to first exacerbation (i.e., reducing the risk of exacerbation) and reducing the frequency of COPD exacerbations.

What is claimed is:

1. A method of treating chronic obstructive pulmonary disease (COPD) in a human subject suffering from COPD who has experienced an exacerbation of COPD, wherein the exacerbation of COPD is a temporary worsening of one or more symptoms of COPD suffered by the human subject lasting at least two consecutive days, the method comprising administering to the human subject via inhalation two or more doses per day of a composition comprising a therapeutically effective amount of ensifentrine or a pharmaceutically acceptable salt thereof, wherein a frequency of the exacerbation of COPD is reduced by at least 40% compared to the frequency of the exacerbation of COPD in an untreated human subject having COPD and not administered the composition, wherein the subject has FEV1 prior to said administering from 30% to 70%, the exacerbation is (a) worsening of 2 or more major symptoms selected from the group consisting of dyspnea, sputum volume, and sputum purulence or (b) worsening of any 1 major symptom selected from the group consisting of dyspnea, sputum volume, and sputum purulence together with a minor symptom selected from the group consisting of sore throat, colds, fever without other cause, and increased cough or wheeze for at least 2 consecutive days, and the therapeutically effective amount of the ensifentrine or the pharmaceutically acceptable salt thereof is 2 mg to 4 mg and wherein the composition is a suspension comprising:

a. ensifentrine particles at a concentration of from 1 to 1.4 mg/ml;

b. polysorbate 20 at a concentration of from 0.3 to 0.7 mg/ml;

c. sorbitan monolaurate at a concentration of from 0 to 0.1 mg/ml;

d. sodium dihydrogen phosphate dihydrate at a concentration of from 0.5 to 1 mg/mL;

e. disodium hydrogen phosphate dihydrate at a concentration of from 0.5 to 1 mg/mL;

f. sodium chloride at a concentration of 5 to 10 mg/mL; and g. water.

2. The method of claim 1, wherein the subject has FEV1 prior to said administering from 30% to 50%.

3. The method of claim 1, wherein the suspension is the only therapeutic composition administered to the subject.

4. The method of claim 1, further comprising administering to the subject one or more additional therapeutic compositions comprising a therapeutic agent selected from the group consisting of long-acting muscarinic antagonists, long-acting beta-agonist, and inhaled corticosteroids, and wherein (i) the one or more additional therapeutic compositions and (ii) the suspension are the only therapeutic compositions administered to the subject.

5. The method of claim 4, wherein the one or more additional therapeutic agents comprises salbutamol.

6. The method of claim 1, wherein a frequency of the exacerbation of COPD is reduced by at least 50% compared to the frequency of the exacerbation of COPD in an untreated human subject having COPD and not administered the composition.

7. The method of claim 1, wherein said administering comprises administering a first dose comprising the therapeutically effective amount of the ensifentrine or the pharmaceutically acceptable dose thereof and a second dose comprising the therapeutically effective amount of the ensifentrine or the pharmaceutically acceptable dose thereof.

8. The method of claim 7, wherein the first dose and the second dose contain an equal amount of the ensifentrine or the pharmaceutically acceptable dose thereof.

9. The method of claim 8, wherein the first dose and the second dose are administered 10 to 14 hours apart.

10. The method of claim 1, wherein the therapeutically effective amount of the ensifentrine or the pharmaceutically acceptable salt thereof is 3 mg.

11. The method of claim 1, wherein said administering is performed via a nebulizer.

12. The method of claim 1, wherein said administering is performed via a pressurized metered dose inhaler.

13. The method of claim 1, wherein said administering is performed for at least 24 weeks.

14. The method of claim 1, wherein the suspension comprises:

a. 1.2 mg/ml of the ensifentrine particles;
b. 0.5 mg/ml of the polysorbate 20;
c. 0.05 mg/ml of the sorbitan monolaurate;
d. 0.744 mg/ml of the sodium dihydrogen phosphate dihydrate;
e. 0.853 mg/ml of the disodium hydrogen phosphate dihydrate;
f. 8.6 mg/ml of the sodium chloride; and
g. water.

* * * * *